United States Patent
Sheldon et al.

(10) Patent No.: US 9,033,880 B2
(45) Date of Patent: *May 19, 2015

(54) ROBOTIC INSERTION SYSTEMS AND METHODS

(75) Inventors: Jeffery J. Sheldon, League City, TX (US); Kenneth R. Smith, League City, TX (US); Bruce W. Dannecker, League City, TX (US); Joseph M. Lacey, Hartselle, AL (US); Katherine E. Goodwin, Houston, TX (US)

(73) Assignee: Houston Medical Robotics, Inc., Houston, TX (US)

( * ) Notice: Subject to any disclaimer, the term of this patent is extended or adjusted under 35 U.S.C. 154(b) by 178 days.

This patent is subject to a terminal disclaimer.

(21) Appl. No.: 13/080,370

(22) Filed: Apr. 5, 2011

(65) Prior Publication Data

US 2012/0259221 A1 Oct. 11, 2012

(51) Int. Cl.
*A61B 8/00* (2006.01)
*A61M 5/42* (2006.01)
*A61M 5/46* (2006.01)
*A61M 25/01* (2006.01)
*A61B 8/08* (2006.01)
(Continued)

(52) U.S. Cl.
CPC ............ *A61B 8/4209* (2013.01); *A61B 8/0891* (2013.01); *A61B 5/15003* (2013.01); *A61M 5/427* (2013.01); *A61B 5/150748* (2013.01); *A61M 5/46* (2013.01); *A61B 5/153* (2013.01); *A61M 25/0105* (2013.01); *A61B 8/0841* (2013.01)

(58) Field of Classification Search
USPC ................................................. 600/407, 437
See application file for complete search history.

(56) References Cited

U.S. PATENT DOCUMENTS

| 4,733,661 A | 3/1988 | Palestrant |
| 4,899,756 A | 2/1990 | Sonek |
| 5,572,999 A | 11/1996 | Funda et al. |

(Continued)

FOREIGN PATENT DOCUMENTS

| WO | 2006120619 | 11/2006 |
| WO | 2010006335 | 1/2010 |

OTHER PUBLICATIONS

Information Disclosure Statement submitted for U.S. Appl. No. 12/502,038, filed Dec. 30, 2009

(Continued)

*Primary Examiner* — Tse Chen
*Assistant Examiner* — Joel F Brutus
(74) *Attorney, Agent, or Firm* — Winstead PC

(57) ABSTRACT

An apparatus for accessing the lumen of a vessel includes a handle providing a controller for operating the apparatus, an image capturing instrument secured to the handle, a display secured to the handle, wherein images captured by the image capturing instrument are displayed on the display, and a robotic platform coupled to the handle. The robotic platform includes a body, a first motor coupled to the body, wherein the first motor adjust the robotic platform to achieve a target insertion depth, and a cartridge carrier pivotally coupled to the body, wherein the robotic platform is adjustable to achieve the target insertion depth. The apparatus also includes a disposable cartridge attached to the cartridge carrier. The disposable cartridge includes a needle slideably coupled to the disposable cartridge, wherein the needle slides to extend to the target insertion depth, and a sheath slideably coupled to the disposable cartridge, wherein the sheath slides to extend to the target insertion depth.

20 Claims, 13 Drawing Sheets

(51) Int. Cl.
*A61B 5/15* (2006.01)
*A61B 5/153* (2006.01)

(56) References Cited

U.S. PATENT DOCUMENTS

| | | | |
|---|---|---|---|
| 5,647,373 | A | 7/1997 | Paltieli |
| 6,193,657 | B1 | 2/2001 | Drapkin |
| 6,695,786 | B2 | 2/2004 | Wang et al. |
| 6,835,193 | B2 | 12/2004 | Epstein et al. |
| 7,166,075 | B2 | 1/2007 | Varghese et al. |
| 7,691,103 | B2 | 4/2010 | Fernandez et al. |
| 7,766,839 | B2 | 8/2010 | Rogers et al. |
| 7,976,469 | B2 | 7/2011 | Bonde et al. |
| 8,066,644 | B2 | 11/2011 | Sarkar et al. |
| 8,235,908 | B2 | 8/2012 | Roschak et al. |
| 2002/0177789 | A1 | 11/2002 | Ferry et al. |
| 2003/0233046 | A1 | 12/2003 | Ferguson et al. |
| 2004/0267121 | A1 | 12/2004 | Sarvazyan et al. |
| 2005/0225448 | A1* | 10/2005 | Schenker .................. 340/573.1 |
| 2006/0111692 | A1 | 5/2006 | Hlavka et al. |
| 2006/0111733 | A1 | 5/2006 | Shriver |
| 2006/0116904 | A1* | 6/2006 | Brem ............................... 705/2 |
| 2007/0135803 | A1 | 6/2007 | Belson |
| 2007/0137372 | A1 | 6/2007 | Devengenzo et al. |
| 2007/0185485 | A1 | 8/2007 | Hauck et al. |
| 2007/0233045 | A1 | 10/2007 | Weitzner et al. |
| 2008/0140087 | A1* | 6/2008 | Barbagli ....................... 606/130 |
| 2008/0146918 | A1 | 6/2008 | Magnin et al. |
| 2008/0167551 | A1* | 7/2008 | Burns et al. .................. 600/427 |
| 2008/0275396 | A1 | 11/2008 | Neerken et al. |
| 2009/0105597 | A1 | 4/2009 | Abraham |
| 2009/0125009 | A1 | 5/2009 | Zikorus et al. |
| 2009/0247993 | A1 | 10/2009 | Kirschenman et al. |
| 2010/0010505 | A1 | 1/2010 | Herlihy et al. |
| 2010/0036245 | A1 | 2/2010 | Yu et al. |
| 2010/0256558 | A1 | 10/2010 | Olson et al. |
| 2012/0197132 | A1 | 8/2012 | O'Connor |
| 2012/0259219 | A1 | 10/2012 | Sheldon et al. |
| 2012/0259220 | A1 | 10/2012 | Sheldon et al. |

OTHER PUBLICATIONS

International Search Report and Written Opinion for PCT/US12/32310 dated Aug. 10, 2012.
International Search Report and Written Opinion for PCT/US12/32346 dated Aug. 3, 2012.
International Search Report and Written Opinion for PCT/US12/32355 dated Aug. 3, 2012.

* cited by examiner

ROBOTIC INSERTION SYSTEMS AND METHODS

STATEMENT REGARDING FEDERALLY SPONSORED RESEARCH

Not Applicable

RELATED APPLICATIONS

Not Applicable

FIELD OF THE INVENTION

This invention relates to imaging assisted access of the lumen of vessels. More particularly, systems and methods discussed herein are related to the placement of a sheath, needle, and/or guidewire in a vessel.

BACKGROUND

Medical treatment may require the placement of catheters or the like into a person's body. For example, central venous catheters (also referred to herein as "CVC") are placed in a large vein for a variety of medical purposes. A series of manually performed steps that have remained largely unchanged to date. First, a hollow introducer needle is manually inserted through the skin and placed in the vein. Second, a guide wire is manually inserted through the hollow of the needle into the lumen of the vein. The guide wire is inserted until a portion of the guide wire extends past the end of the needle. In this position, the distal end of the wire is in the central vein and the proximal end is outside the patient's body. The introducer needle, which at this point has the guide wire running through its length, is then removed from the patient by pulling the needle out and over the wire. During removal of the needle, the distal end of the guide wire is undisturbed inside the lumen of vein. Third, the hollow CVC is placed over the proximal end of the guide wire, and the CVC advanced along the wire, through the skin, the subcutaneous tissues, and into the vein. At its final position, the catheter will have one end in the vein and the other end outside of the body. The guide wire can now be retrieved by pulling the guide wire through the catheter and out of the body, without disturbing the position of the catheter. The catheter can now be used to access to the central venous circulation. This process relies on the medical practitioner to locate the vein and may require several attempts before the CVC is properly placed. Similarly, other medical procedures may require placement of a sheath, needle, and/or guidewire into the lumen of a vessel. Medical practitioners may encounter similar problems when attempting to place a sheath, needle, and/or guidewire into the lumen of a vessel.

More recently, ultrasound has been used to assist in the placement of a CVC in a vein. Ultrasound can used to locate the venous lumen and provide a visual target. The CVC may be placed manually or a robotic device may be used to place the CVC. Even with ultrasound guidance, a medical practitioner may fail to properly place the CVC. Further, current robotic devices are significantly large, cumbersome, and costly and their use in the placement of CVC is impractical.

SUMMARY

In one implementation, an apparatus for accessing the lumen of a vessel includes a handle providing a controller for operating the apparatus, an image capturing instrument secured to the handle, a display secured to the handle, wherein images captured by the image capturing instrument are displayed on the display, and a robotic platform coupled to the handle. The robotic platform includes a body, a first motor coupled to the body, wherein the first motor adjust the robotic platform to achieve a target insertion depth, and a cartridge carrier pivotally coupled to the body, wherein the robotic platform is adjustable to achieve the target insertion depth. The apparatus also includes a disposable cartridge attached to the cartridge carrier. The disposable cartridge includes a needle slideably coupled to the disposable cartridge, wherein the needle slides to extend to the target insertion depth, and a sheath slidably coupled to the disposable cartridge, wherein the sheath slides to extend to the target insertion depth.

In another implementation, a method for accessing the lumen of a vessel includes the steps of attaching a disposable cartridge to the robotic platform. The robotic platform includes a body, a first motor coupled to the body, wherein the first motor adjust the robotic platform to achieve a target insertion depth, and a cartridge carrier pivotally coupled to the body, wherein the robotic platform is adjustable to achieve the target insertion depth. The method further includes placing the robotic platform over a target vessel, wherein an image capturing device generates an image of the target vessel on a display; selecting the target vessel on the display, wherein a depth of the target vessel is measured when selected; and actuating an actuator a first time, wherein actuating the actuator the first time causes a needle or a sheath provided in the disposable cartridge to advance to the depth measure and into the target vessel.

In yet another implementation, an insertion system includes a handle providing a controller for operating the system, an image capturing instrument secured to the handle, a display secured to the handle, wherein images captured by the image capturing instrument are displayed on the display, and a robotic platform coupled to the handle. The robotic platform automatically adjust to achieve a target insertion depth, and a disposable cartridge is pivotally attached to the robotic platform. The disposable cartridge provides a sheath, a needle, and a guidewire. The robotic platform inserts the sheath, needle, or guidewire to the target insertion depth.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1A:
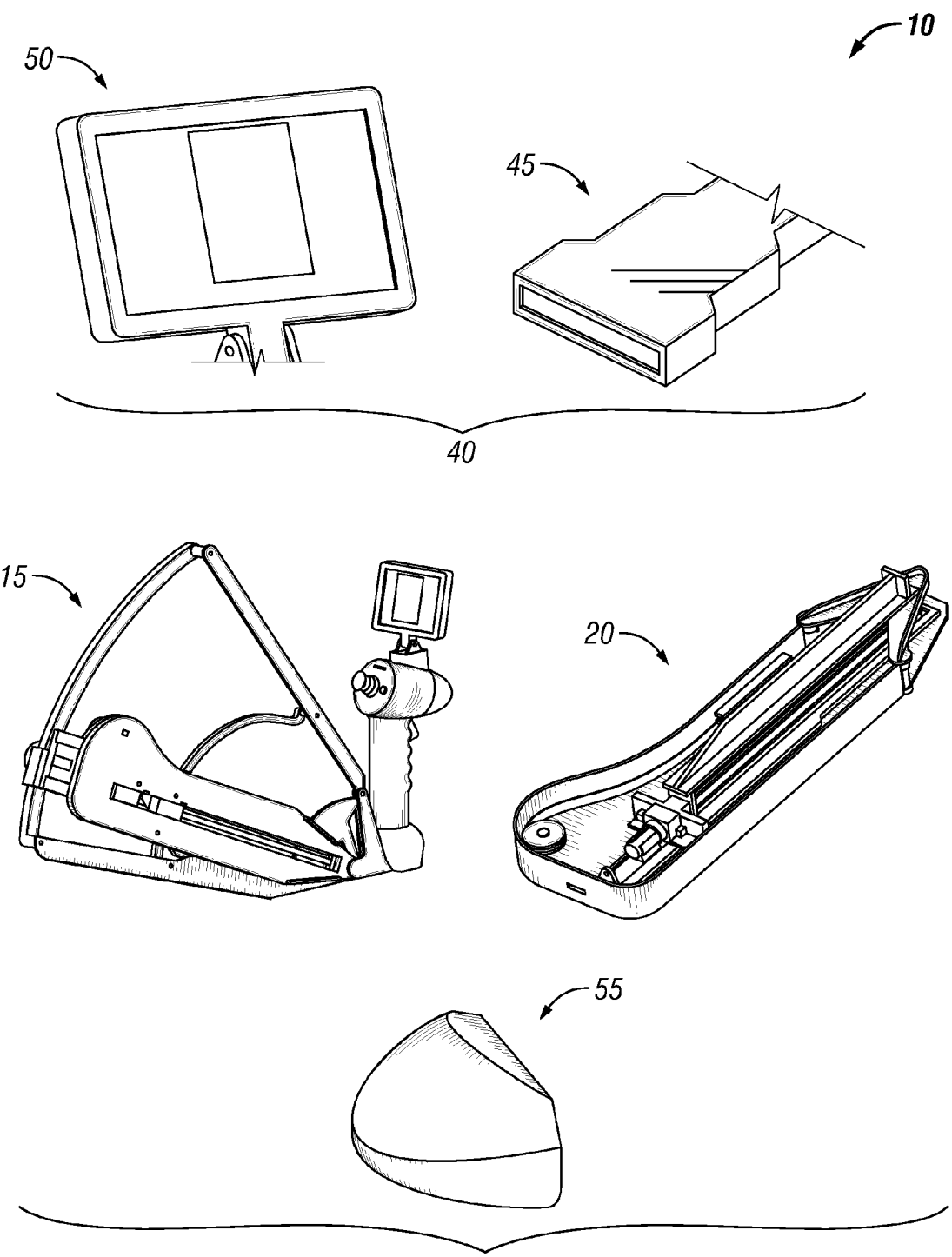
FIGS. 1A and 1B are an illustrative implementation of a robotic insertion system.

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The systems and methods discussed herein are designed to incorporate an insertion system with an imaging system (e.g. ultrasound system) to provide a medical practitioner with the capability to accurately and reliably accessing the lumen of a vessel located at a depth of 5 mm to 60 mm below the skin surface. For example, the systems and methods discussed herein may be utilized to place a central venous catheter (CVC). While the implementations discussed herein may discuss usage of the systems and methods for starting a CVC, it will be recognized by one of ordinary skill in the art that the scope of the invention is in no way limited to starting a CVC. For example, in other implementations, the system may be utilized to place needle in a vessel; to place a guidewire via a needle placed in a vessel; or to place a sheath via a guidewire that is placed in a vessel via a needle. The systems and methods discussed herein may be utilized in a variety of medical procedures, including, but not limited to: CVC placement, peripherally inserted central catheters, phlebotomy, dialysis access, cardiac catheterization, amniocentesis, cholecystotomy, thoracentesis, paracentesis, and tracheostomy. The insertion system is portable, reusable, robotic, and easily operated.

Figure 1B:
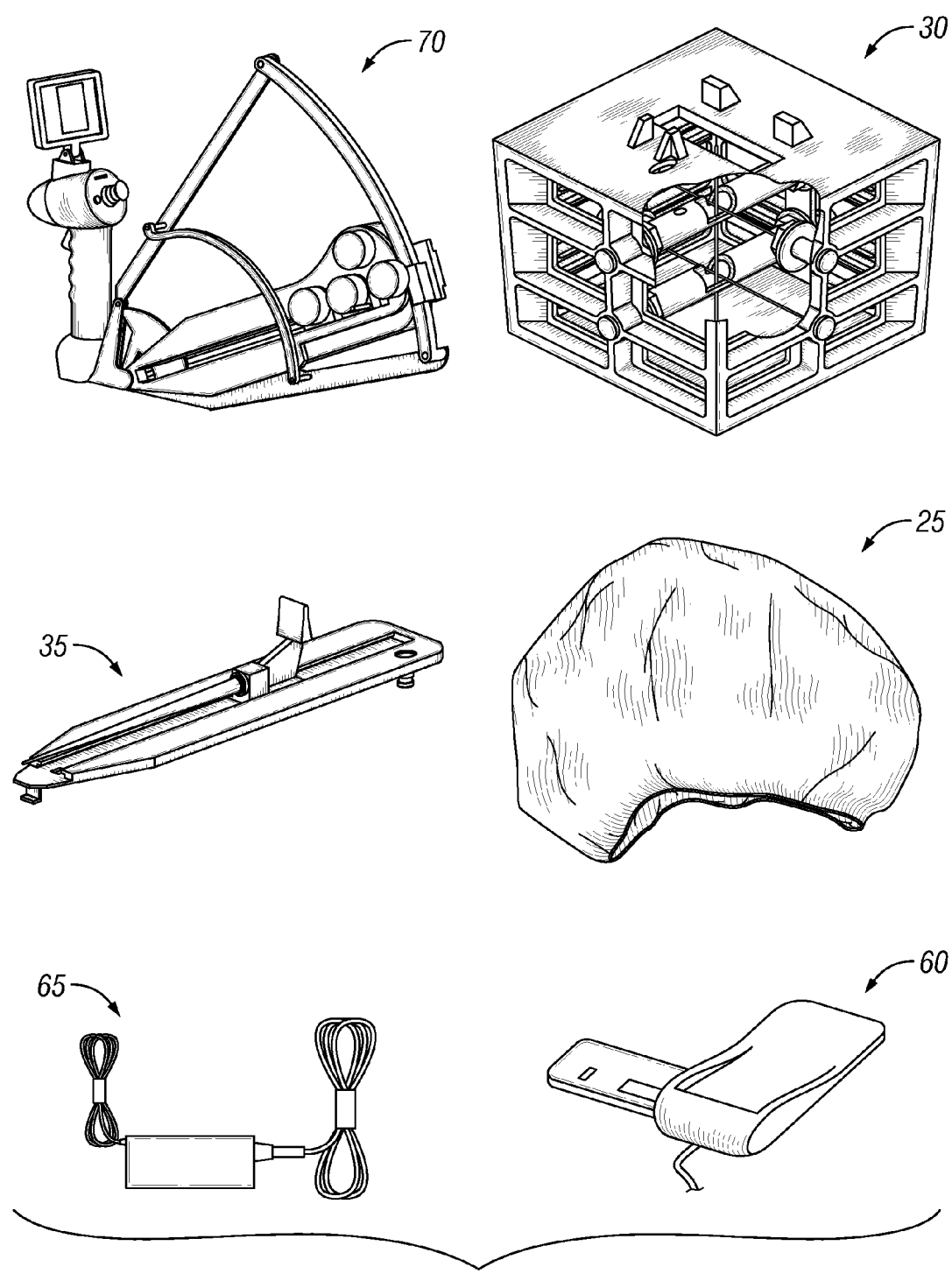

FIGS. 1A and 1B are an illustrative implementation of a robotic insertion system 10. Robotic insertion system 10 may include a robotic platform 15, disposable cartridge 20, cover 25, imaging capturing instrument 45, display 50, docking platform 60, and external power adapter/cable 65. Robotic insertion system 10 is combined with a portable imaging device 40 that may include an image capturing instrument 45 and image display 50. For example, imaging device 40 may be an ultrasound imaging device with a transducer utilized to capture images and a display presenting the captured images. Imaging device 40 is combined with robotic platform 15 so that no additional equipment is needed for robotic insertion system 10.

Robotic platform 15 provides a platform that receives several components that are utilized during the sheath insertion process to form a handheld robotic device 70. For example, disposable cartridge 20, imaging capturing instrument 45, display 50, and/or rechargeable battery 55 may be attached or coupled to robotic platform 15 during various steps in the insertion process. Some components, such as disposable cartridge 20 and rechargeable battery 55, are designed to be easily attached and removed from robotic platform 15 due to repeated removal and attachment of such components. Other components, such as imaging capturing instrument 45 and display 50, are attached in a secure manner. Robotic platform 15 utilized several motors to move, adjust, and control components of robotic insertion system 10 during the insertion process as discussed herein.

Disposable cartridge 20 can be coupled to robotic platform 15 and may include a needle, guidewire, catheter, and other components utilized to place a CVC or the like. Cover 25 is sterile and may be place on robotic platform 15 to prevent contamination or the like. Cover 25 may be placed on or around robotic platform 15 and disposed of after usage. Robotic platform 15 may be capable of self or internal calibration to maintain a desired level of accuracy in robotic insertion system 10. However, in some implementations, alignment cube 30 and alignment cartridge 35 can be coupled to robotic platform 15 and may be utilized to perform a check on the alignment of robotic platform 15. Docking platform 60 may receive handheld robotic device 70 when the device is not in use. Docking platform 60 may provide electrical connectors that mate with connectors provided on handheld robotic device 70, thereby allowing rechargeable battery 55 to be recharged when placed on the docking platform. Docking platform 60 may also provide a keyboard utilized to input data, such as patient information, that is sent to handheld robotic device 70 through the electrical connectors and stored in memory. External power adapter/cable 65 is utilized to power handheld robotic device 70 and/or charge rechargeable battery 55. A first end of external power adapter/cable 65 may be mated to an AC power source. The external power adapter/cable 65 converts the AC power to DC power suitable for powering the device and charging the battery. The second end of external power adapter/cable 65 may be connected directly to handheld robotic device 70 or docking platform 60.

Figure 2A:
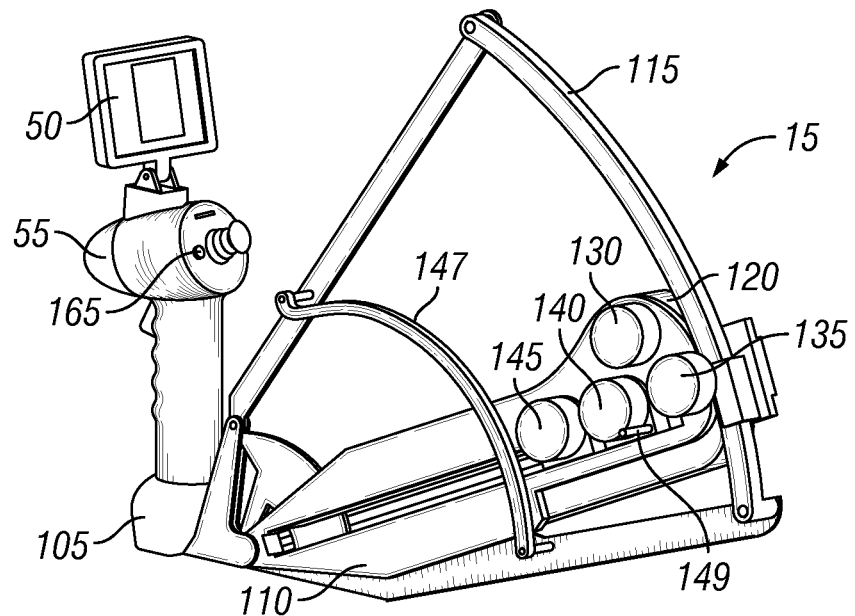
FIGS. 2A and 2B are illustrative implementations of a handheld robotic device.
Figure 2B:
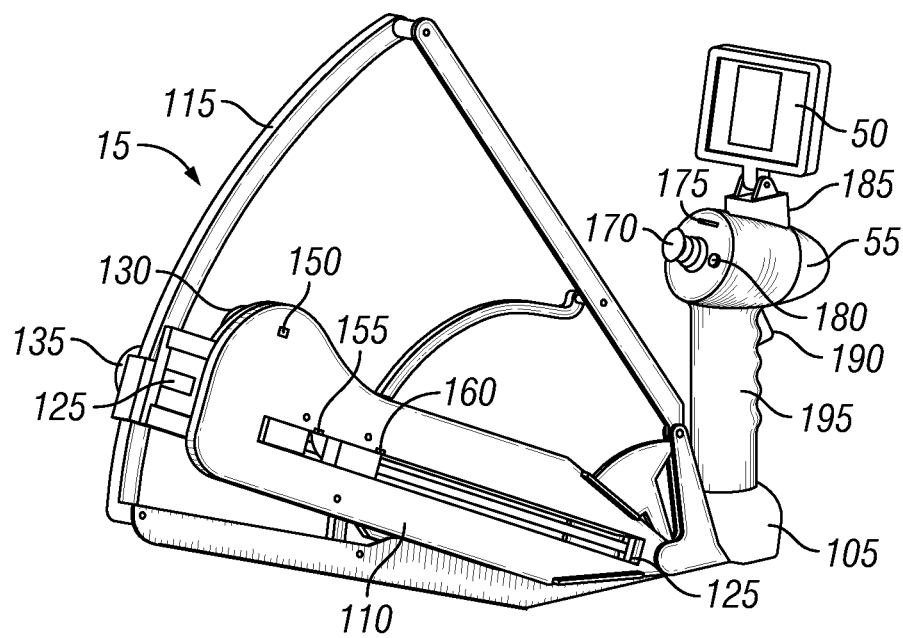

FIGS. 2A and 2B are illustrative implementations of a handheld robotic device 70. For the purposes of illustration and clarity, robotic platform 15 is shown without a cover and display in some implementations. Robotic platform 15 may include a transducer housing 105, cartridge carrier 110, arc arm 115, cartridge 120, attachment points 125, guidewire motor 130, angle motor 135, needle motor 140, sheath motor 145, guidewire actuator 150, needle actuator 155, sheath actuator 160, data entry mode button 165, thumb control 170, memory card slot 175, operation mode button 180, display support 185, trigger control 190, and ergonomic handle 195.

Transducer housing 105 provided at the base of ergonomic handle 195 houses image capturing instrument 45 of imaging device 40 and secures it to robotic platform 15. For example, an ultrasound transducer may be secured to robotic platform 15 in transducer housing 105. Robotic platform 15 may provide attachment points 125 to hold and support cartridge 120 on cartridge carrier 110. Cartridge 120 may be an alignment cartridge or disposable cartridge. A first end of cartridge carrier 110 is pivotally attached to robotic platform 15 near transducer housing 105. The opposite end of cartridge carrier 110 is coupled to arc arm 115. Angle motor 135 on cartridge carrier 110 may be coupled to arc arm 115 as well to adjust the angle of cartridge carrier 110. For example, angle motor 135 may be coupled to a gear or wheel that rotates to adjust the angle of arc arm 115. Further, arc arm 115 may include gear teeth that mate with the teeth on the gear or wheel coupled to angle motor 135. Arc arm 115 may provide depth scale indicating the depth of insertion for a particular angle of cartridge carrier 110. In other implementations, cartridge carrier 110 may be capable of adjusting laterally, in addition to, or instead of rotating about a pivot point. Motor 135 or a combination of motors may adjust cartridge carrier 110 laterally. Note that cartridge carrier 110 is disposed within arc arm 115 close to transducer housing 105. By placing cartridge carrier 110 near ergonomic handle 195, the weight of handheld robotic device 70 is shifted closer to where an operator grasp the device. This makes handheld robotic device 70 more balanced and easier to manage for the operator.

Guidewire motor 130 is coupled to guidewire actuator 150 on cartridge carrier 110. When a cartridge 120 with a guidewire is properly attached to cartridge carrier 110, guidewire motor 130 may actuate guidewire actuator 150 to advance or retract the guidewire. Needle motor 140 is coupled to needle actuator 155 on cartridge carrier 110. When a cartridge 120 with a needle is properly attached to cartridge carrier 110, needle motor 140 may actuate needle actuator 155 to advance or retract the needle. Sheath motor 145 is coupled to sheath actuator 160 on cartridge carrier 110. When a cartridge 120 with a sheath is properly attached to cartridge carrier 110, sheath motor 145 may actuate needle actuator 160 to advance or retract the sheath. A stop bar 147 is provided by robotic platform 15. Stop bar 147 is an arc-like bar positioned on robotic platform 15 between transducer housing 105 and arc arm 115. An extension 149 extends from needle actuator 155. As shown, stop bar 147 is positioned along the pathway of needle actuator 155 so that extension 149 will contact stop bar 147 when the needle actuator 155 is advanced forward. In another implementation, cartridge 120 may be an alignment cartridge that does not provide a guidewire, needle, and sheath. The alignment cartridge may provide a stylet that represents the needle and/or sheath during an alignment check. Needle actuator 155 or sheath actuator 160 may be coupled to the stylet when the alignment cartridge is attached to cartridge carrier 110.

Guidewire motor 130, angle motor 135, needle motor 140, and sheath motor 145 may be coupled to a power source. For example, robotic platform 15 may include a rechargeable battery 55 or robotic platform 15 may attach to an external power adapter/cable 65 that can be plugged into a power outlet. Robotic platform 15 may provide a connector (not shown) that can be connected to external power adapter/cable 65 when necessary. A connector plug (not shown) may be provided to protect the connector when it is not in use. External power adapter/cable 65 provides an AC connector that can be connected to an AC power source. External power adapter/cable 65 converts the AC power to DC power for robotic platform 15. External power adapter/cable 65 also provides a connector that allows the adapter/cable to be connected to robotic platform 15 or docking platform 60. When the connector is attached to docking platform 60 and robotic platform 15 is placed on docking platform 60, rechargeable batteries 55 in handheld robotic device 70 are recharged by docking platform 60. When external power adapter/cable 65 is connected directly to handheld robotic device 70, rechargeable batteries 55 are recharged and/or the device can be powered directly from the adapter/cable 65.

Data entry mode button 165 allows an operator to enter and exit a data entry mode, which allows data to be entered and stored by the device. Operation mode button 180 allows the operator to enter and exit operation mode(s). Thumb control 170 is utilized to operate, navigate, and make selections. For example, various options may be provided in a menu or the like on display 50, wherein the operator selects from the menu utilizing thumb control 170. The operator may navigated the menu with thumb control 170 and make a selection by pressing thumb control 170 directly into robotic platform 15. Memory card slot 175 allows a memory card to be inserted into robotic platform 15 to store desired information, such as patient data, ultrasound video, and the like. In some implementations, a memory may be provided in ergonomic handle 195 allowing the user to choose to store directly to robotic platform 15 or the memory card. Trigger control 190 may be utilized to activate needle insertion, sheath insertion, needle retraction, guidewire insertion, and the like. Robotic platform 15 includes an ergonomic handle 195 providing comfortable handling of the device during usage.

Display 50 is attached to the top of ergonomic handle 195 by display support 185. Display support 185 allows the angle of display 50 to be adjusted as desired. Further, in some implementations, display support 185 may allow the display 50 to swivel as well. A wiring harness (not shown) may be provided in ergonomic handle 195 to connect various electronic components in robotic platform 15.

The robotic platform may also contain a programmable Central Processing Unit (CPU) or microprocessor or Field-Programmable Gate Arrays (FPGAs), motor controller(s), force sensors (load cells), visual/audible indicators/alert signals and video electronics. In some implementations, programmable microprocessor or FPGA(s), motor controller(s), visual/audible indicators/alert signals, memory card reader/writer and video electronics may be integrated into the ultrasound device display. The CPU, microprocessor, or FPGA(s) may be loaded with software/firmware that provides the logic to perform all required functions. CPU, microprocessor, or FPGA(s) may be coupled to the electronic components of the device, such as imaging device 40, rechargeable battery 55, various motors, various controllers, memory, and the like. Motor controller(s) and visual/audible indicators/alert signals may react to signals from sensors to provide feedback and/or haptics to an operator.

Figure 3A:
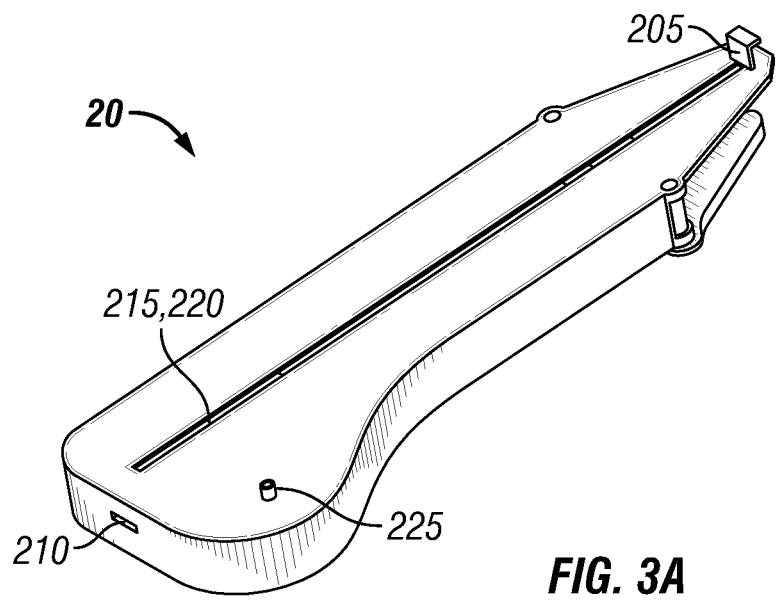
FIGS. 3A and 3B are illustrative implementations of a disposable cartridge.
Figure 3B:
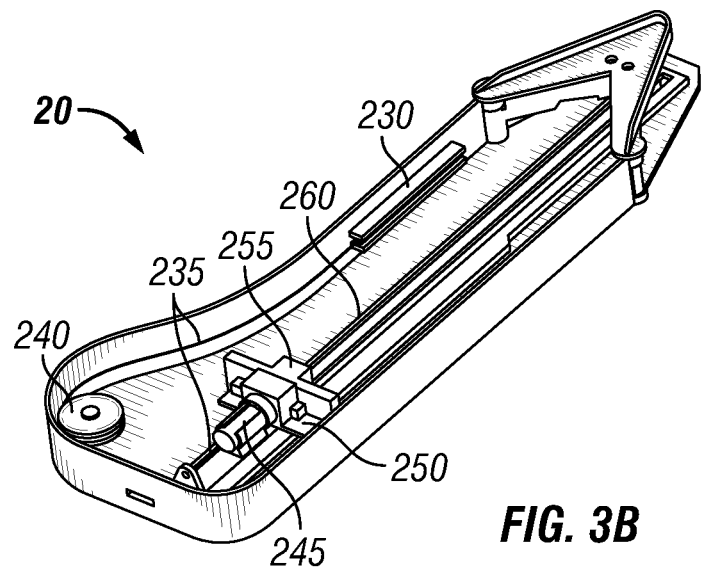

FIGS. 3A and 3B are illustrative implementations of a disposable cartridge 20. Disposable cartridge 20 may be enclosed in a clear sterile cover, but the cover is not shown in the figures for the purpose of illustration. For example, the cover may be a clear sterile polymer, Tyvek®, or any suitable material or combination of materials. Disposable cartridge 20 is sterile to prevent the spread of bacteria, disease, etc. Disposable cartridge 20 is disposed after a single use. However, in other implementations, a cartridge may be subject to a cleaning and disinfection process after each use. Disposable cartridge 20 may include an attachment bracket 205, attachment slot 210, needle interface 215, sheath interface 220, guidewire interface 225, guidewire track 230, guidewire 235, guidewire wheel 240, needle hub 245, sliding truck 250, sheath hub 255, sheath 260, and needle 262. Attachment bracket 205 and attachment slot 210 are utilized to secured disposable cartridge 20 to cartridge carrier 110. Needle interface 215 and sheath interface 220 of disposable cartridge 20 mate with needle actuator 155 and sheath actuator 160 of cartridge carrier 110. This allows needle actuator 155 in cartridge carrier 110 to move a needle in disposable cartridge 20 and sheath actuator 160 in cartridge carrier 110 to move sheath 260 in disposable cartridge 20. Guidewire interface 225 mates with guidewire actuator 150, thereby allowing guidewire motor 130 to advance and retract guidewire 235.

Guidewire 235 passes through guidewire track 230 to guidewire wheel 240, which advances or retracts guidewire 235. Guidewire 235 passes through the center of needle hub 245 down through the center of sheath 260 and needle 262. Needle 262 is positioned in the center of sheath 260 and may slide into and out of sheath 260. In some implementations, a dilator may be provide in between needle 262 and sheath 260 to minimize or prevent bending of needle 262. Needle hub 245 is attached to needle interface 215, sliding truck 250, and the needle 262. When needle interface 215 is advanced or retracted by needle motor 140, it causes the needle 262, needle interface 215, and sliding truck 250 to advance or retract as well. Sheath hub 255 is connected to sheath 260 and sheath interface 220. When sheath motor 140 advances or retracts sheath interface 220, it causes the sheath hub 255 and sheath 260 to advance or retract as well. Note, sliding truck 250 and sheath hub 255 are not connected. Because sliding truck 250 and sheath hub 255 travel along the same path, advancing sliding truck 250 into sheath hub 255 also causes the sheath hub to advance. However, retracting sliding truck 250 does not cause sheath hub 255 to retract.

Figure 4:
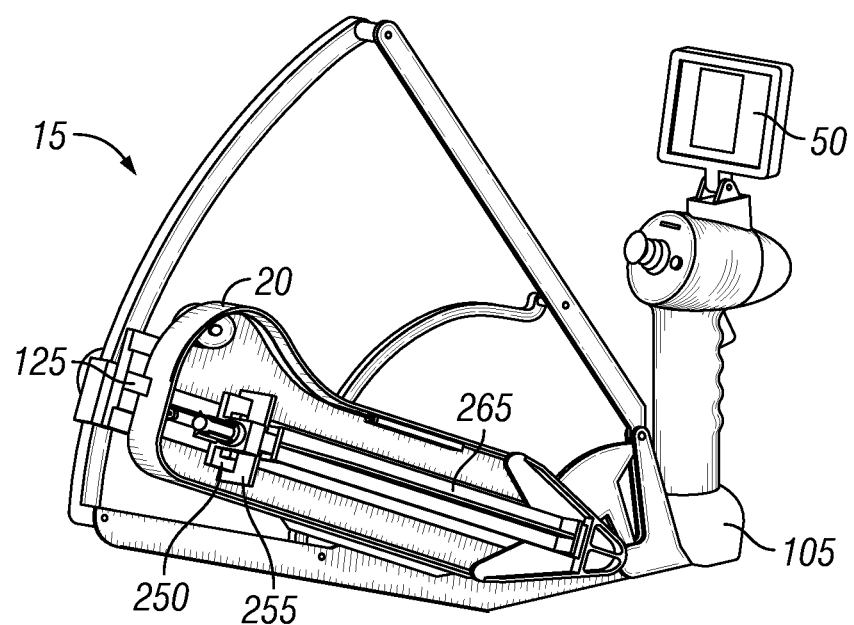
FIG. 4 is an illustrative implementation of a handheld robotic device with a disposable cartridge attached.

FIG. 4 is an illustrative implementation of a disposable cartridge 20 placed in handheld robotic device 70. Lock bar 265 is designed to secure sheath 260, needle 262, and/or associated medical components in a desired position to prevent undesired movement before the lock bar is removed. Lock bar 265 prevents sliding truck 250 and sheath hub 255 from advancing in disposable cartridge 20. For example, during shipping, before attachment to the robotic platform, and/or prior to use it is desirable to prevent a sharp needle and sheath from protruding from disposable cartridge 20. Further, this prevents potential contamination of disposable cartridge 20 prior to use. However, when disposable cartridge 20 is attached to robotic platform 20 that is ready for use, lock bar 265 may be removed to allow sliding truck 250, sheath hub 255, and associated medical components to be freely advanced and retracted. Attachment point 125 is a clip that is utilized to secure disposable cartridge 20 to robotic platform 15. Attachment point 125 fits into attachment slot 210 on disposable cartridge 20 when properly attached. The second attachment point 125 (not shown) mates with attachment bracket 205 provided by disposable cartridge 20. Image capturing instrument 45 provided in transducer housing 105 will preferably be capable of imaging and measuring depths of approximately 5 mm to 60 mm that are shown on display 50.

Figure 5:
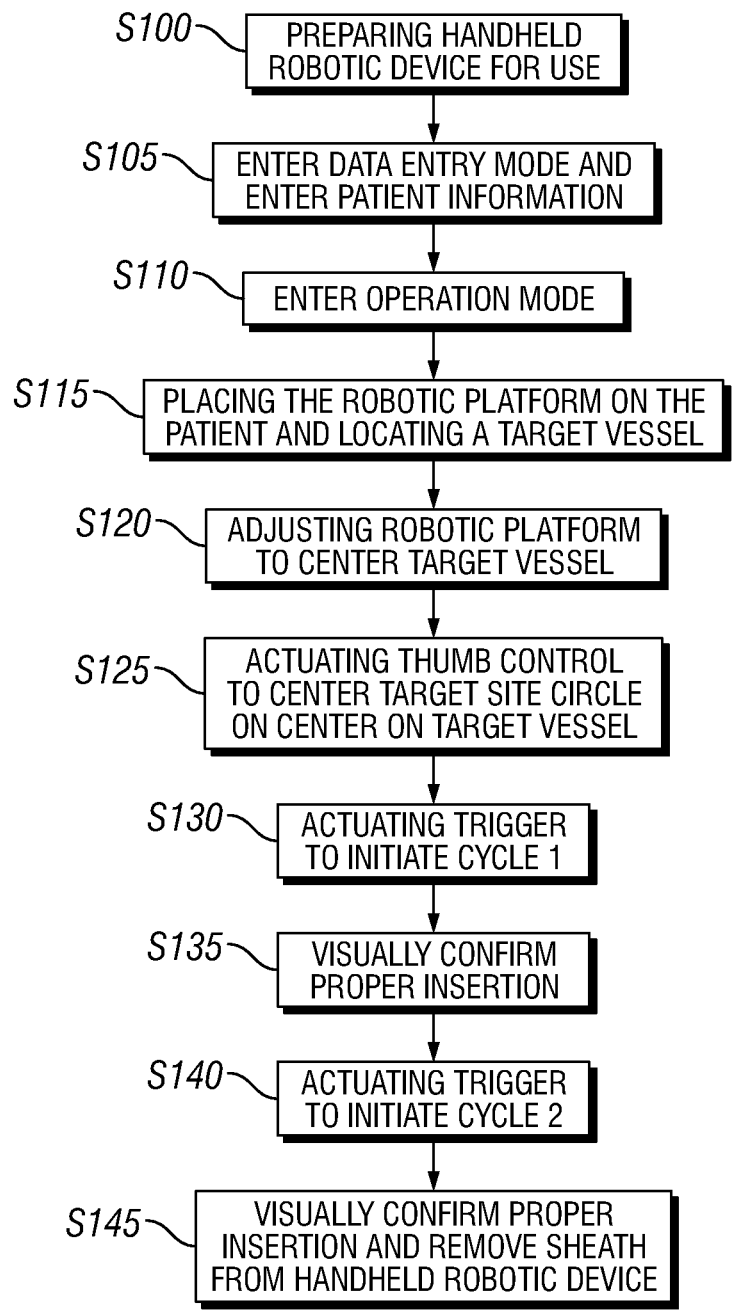
FIG. 5 is an illustrative implementation of a method for inserting a sheath into a vessel with a robotic sheath insertion device.

FIG. 5 is an illustrative implementation of a method for inserting a sheath into a vessel with a robotic insertion system. Many of the steps for the method discussed herein may be performed in a different sequence than shown or may be omitted. The scope of methods for inserting a sheath into a vessel is in no way limited to the particular methods illustrated herein. One of ordinary skill in the art will recognize a variety of potential variations in the sequence and particular steps performed. While the following provides a description of inserting a sheath into a vessel, it will be recognized by one of ordinary skill in the art that the device is suitable for a variety of medical procedures involving the insertion of a sheath, needle, and/or guidewire into the lumen of a vessel. The scope of the claims is in no way limited to inserting a sheath into a vessel, except where expressly stated in the claims. For example, in other implementations, the insertion system may simply be utilized to place a needle in the lumen of a vessel or to place a guidewire in the lumen of a vessel with the aid of a needle.

The following description assumes that the patient has been prepared to receive the procedure and rechargeable battery 55 is fully charged and attached to handheld robotic device 70. To prepare the device for use in step S100, the operator installs the memory card (optional), attaches disposable cartridge 20 to handheld robotic device 70, and places sterile cover 25 over handheld robotic device 70. Once this has been completed, the operator may then power on the handheld robotic device.

After powering on handheld robotic device 70, the operator enters the data entry mode in step S105 using data entry mode button 165. This activates the data entry software and menus appear allowing the operator to enter and store the patient information. Handheld robotic device 70 may include a keyboard interface that will allow the operator to enter patient information to be stored on the memory card. The keyboard may be provided via thumb control 170 selection of a keyboard displayed on display 50 or via or physical keys mounted on robotic platform 15 or docking platform 60. The patient data entered by the operator will be stored on the memory card. In other implementations, the operator may want to skip the data entry step and may proceed directly to the next step.

Figure 8:
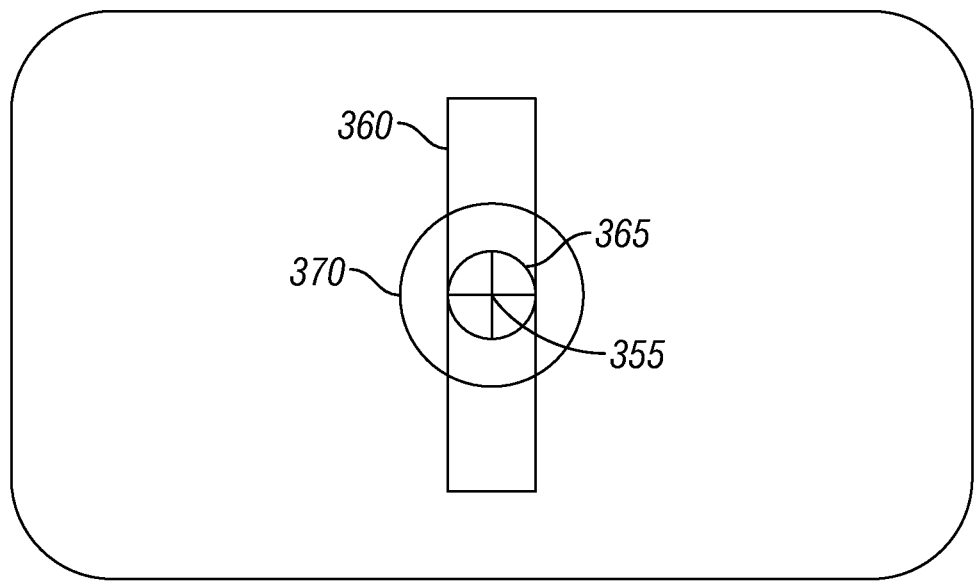
FIG. 8 is an illustrative implementation of a image displayed on a display when a handheld robotic device is placed on a target vessel.

After entering the patient data, the operator exits data entry mode and changes the handheld robotic device to operation mode by actuating operation mode button 180 in step S110. Once the device is in operation mode, video recording of the video image displayed on display 50 is activated. Upon entering operation mode, the operator places handheld robotic device 70 on the patient near a desired location in step 5115. By monitoring display 50 and moving handheld robotic device 70, the operator may locate a candidate vessel for the sheath insertion procedure to be performed on. For example, FIG. 8 provides an illustrative implementation of an image displayed on display 50 during operation of handheld robotic device 70.

The operator adjusts the position of handheld robotic device 70 to center the device on the target vessel in step S120. In particular, the operator adjust handheld robotic device 70 until the rectangular target site boundary is centered and placed on the selected vessel, as shown in FIG. 8. The operator may move the thumb control 170 to place the target site circle on the vessel in step S125. If the vessel walls (shown by the larger circle) do not exceed the diameter of the target site circle (shown by the smaller circle), the vessel is not larger than 4 mm in diameter and is no longer a candidate for the sheath insertion procedure. The operator must then select a different vessel or a different place along the vessel by moving handheld robotic device 70. If the vessel walls exceed the diameter of the target site circle, the vessel is acceptable or large enough for the sheath insertion procedure. Once the operator confirms that the candidate vessel is large enough, the operator may complete step S125 by centering the target site on the center of the vessel, as shown in FIG. 8. When this position is achieved, handheld robotic device 70 can properly calculate the depth of the vessel. Next, the operator can actuate trigger control 190 once to initiate cycle 1 in step S130. During cycle 1, handheld robotic device 70 adjust the device to achieve the target depth of the vessel and inserts the needle to the target depth within the target vessel. For example, the CPU may control the angle motor or the like to adjust the cartridge carrier to achieve the target depth. Handheld robotic device 70 subsequently inserts 3 mm of guidewire 235 into the vessel. Handheld robotic device 70 then displays a visual and/or audible indication that cycle 1 is complete and another message requesting the operator to verify insertion. The operator may then evaluate the ultrasound image on display 50 and determine if the current state is acceptable to continue the procedure in step S135. If the operator determines the current state is acceptable, the operator may then actuate trigger control 190 a second time to initiate cycle 2 in step S140. Handheld robotic device 70 provides a visual and/or audible indicator that cycle 2 is activated and fully advance guidewire 235. Once guidewire 235 is at full length, handheld robotic device 70 will fully advance sheath 260 into the patient's vessel. Handheld robotic device 70 may then fully retract the needle and fully retract guidewire 235 leaving sheath 260 in the patient's vessel. Handheld robotic device 70 may then provide a visual and/or audible indication that cycle 2 is complete. Once cycle 2 is complete, video recording automatically terminates. In some implementations, during execution of cycle 2, an option to leave the guidewire 235 in the sheath/patient at the end of the cycle may also be provided. The operator may then visually verify sheath insertion on display 50 and remove the proximal end of the sheath from handheld robotic device 70 leaving the sheath correctly inserted in the patient in step S145.

During execution of cycle 1, the seal of the sterile disposable cartridge will be broken only at the needle penetration and extraction point minimizing the external contaminants that entering the sterile disposable cartridge during operation of the device. The handheld robotic device will also contain a mechanism that will sense excessive insertion force of the needle and guidewire and automatically stop the advancement of the needle and guidewire if a predefined limit is reached. This will automatically stop the insertion of a needle in the event that the needle inadvertently contacts a dense object, such as a bone or tendon, and prevent patient complications associated with incorrect insertion of a medical component.

The handheld robotic device will be portable and battery operated, providing the option to operate using battery 55 or using an external power adapter/cable 65. The docking platform 60 will have attachment points to secure the device and electrical connection points to recharge the onboard battery system and transfer data to and from the device. Operating the handheld robotic device using external power will require connecting one end of the external power adapter/cable 65 to an external power outlet and the other end of the adapter/cable to the handheld robotic device 70. Additionally, the battery 55 may also recharge while the device is operating on external power.

An alignment check may be performed to check the alignment of the insertion system. In particular, the alignment check may be performed to ensure the mechanical structure and sliders on the robotic platform 15 are in correct positions. Robotic platform 15 may be capable of providing self or internal calibration to maintain a desired level of accuracy.

Figure 6:
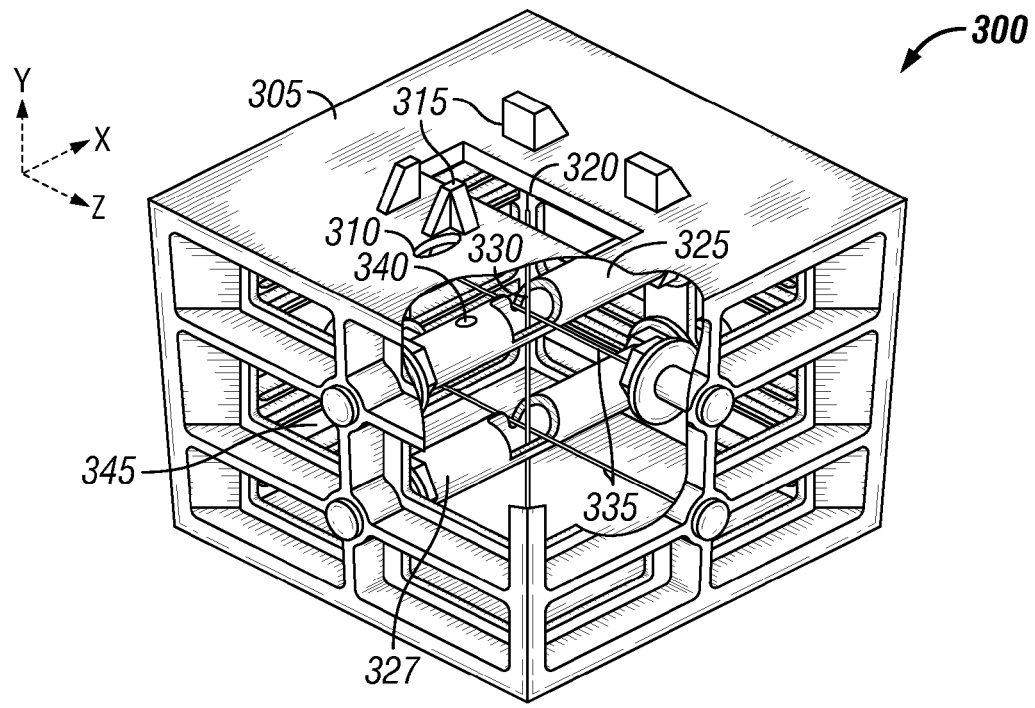
FIG. 6 is an illustrative implementation of an alignment cube.

In other implementations, robotic platform may utilize an alignment cube 300 to perform alignment check(s). FIG. 6 is an illustrative implementation of an alignment cube 300. Alignment cube 300 enables the operator to perform alignment tasks. Top lid 305 of alignment cube 300 provides a needle insertion port 310, alignment guides 315, and image capturing window 320. Needle insertion port 310 provides an entry point for the needle/stylet to enter alignment cube 300. Alignment guides 315 receive transducer housing 105 of handheld robotic device 70. Image capturing window 320 provides an opening for the image capturing instrument 45 of the imaging device 40. Image capturing window 320 is directly above the target points of shallow vessel target (X-Axis) 325 and deep vessel target (X-Axis) 327 in alignment cube 300.

Shallow vessel target 325 is positioned at a depth of 30 mm and deep vessel target 327 is positioned at a depth of 60 mm. Vessel targets 325, 327 are arranged to travel along the x-axis of alignment cube 300. Each vessel target 325, 327 in the alignment cube includes a premeasured and marked target center point. In particular, the target center points are indicated by wire structures intersecting in vessel targets 325, 327. Target wire 330 is arranged vertically or along the y-axis in alignment cube 300. Target wires 335 are arranged perpendicular to vessel targets 325, 327 along the z-axis in alignment cube 300. Target wires 335 are perpendicular to vessel targets 325, 327 and target wire 330. Shallow vessel target 325 at a depth of 30 mm may include a needle/stylet window 340 that allows the needle/stylet to pass through to the top vessel. This needle/stylet window 340 allows the needle/stylet to reach deep vessel target 327 at a depth of 60 mm. Alignment cube 300 may include several viewing windows 345, or the sides of the cube may be made of a transparent material, to allow a operator to view the alignment process of the insertion system. Alignment cube 300 and vessel targets 325, 327 can be filled with water by the operator to accommodate the imaging signal.

Figure 7:
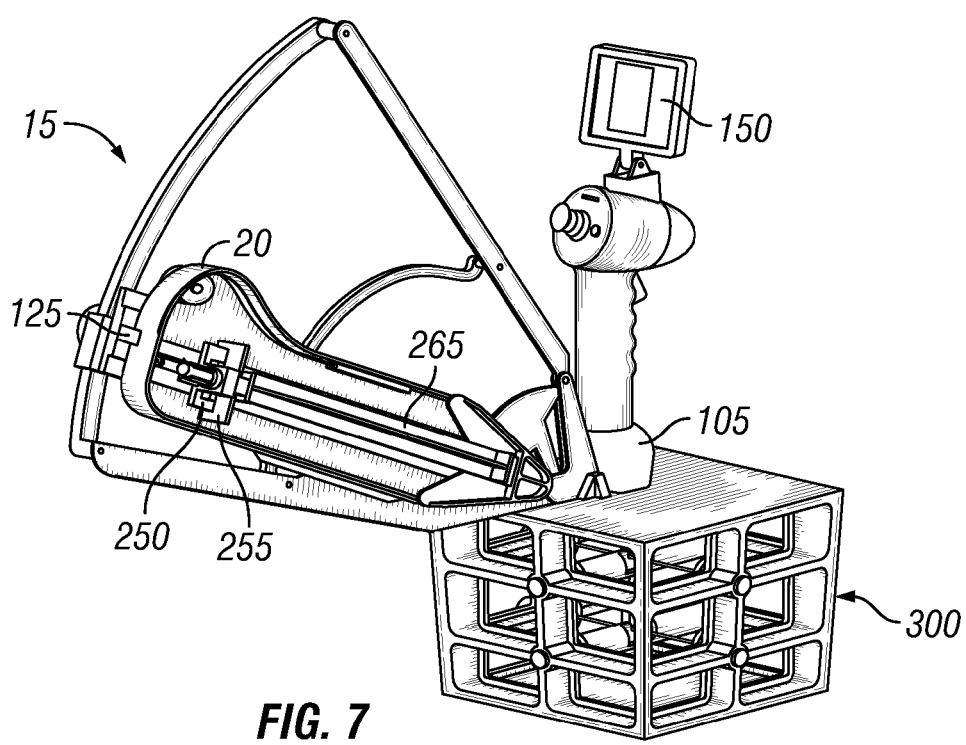
FIG. 7 is an illustrative implementation of a handheld robotic device placed on top of an alignment cube.

FIG. 7 is an illustrative implementation of a handheld robotic device 70 placed on top of an alignment cube 300. Note that image capturing instrument 45 and robotic platform 15 may be cleaned and disinfected prior to the first alignment check. After filling the alignment cube with water, the robotic platform 15 may be placed on top of the alignment cube.

FIG. 8 is an illustrative implementation of a image displayed on display 50 when handheld robotic device 70 is placed near a target vessel. When robotic platform 15 is properly aligned, the image resulting from placing handheld robotic device 70 on top of a target vessel 370 should resemble FIG. 8. Display 50 will show a target site 355 and a target site boundary 360 generated by handheld robotic device 70 and a target vessel 370 generated by image capturing instrument 45. Target site 355 and target site boundary 360 are utilized setup and control handheld robotic device 70 to operate to a desired target depth. Target vessel 370 represents an image generated by imaging device 40 when handheld robotic device 70 is place on a cylindrical-shaped vessel, such as a target vessel in a patient. Target site 355 provides crosshairs and a target site circle 365 that represents the minimum vessel size suitable for handheld robotic device 70. Target site boundary 360 is a rectangle that represents the suitable depths that handheld robotic device 70 should be utilized for and represents an area that components of the device are operable within. For example, handheld robotic device 70 cannot extend needle and/or sheath outside of target site boundary 360 when properly aligned. Target site boundary 360 remains in the same position and centered on display 50. However, target site 355 can be adjusted up and down within target site boundary 360 to achieve different insertion depths. For example, thumb control 170 may be utilized to adjust the position of target site 355. Target vessel 370 is a circle that represents an image that is generated by image capturing instrument 45 when handheld robotic device 70 is placed on a vessel, such as a patient's vessel or vessel targets 325 in alignment cube 300. When target site 355 and target site boundary 360 are properly centered on target vessel 370, handheld robotic device 70 can calculate the depth of target vessel 370 and automatically adjust cartridge carrier 110 to achieve the desired insertion depth.

Figure 9:
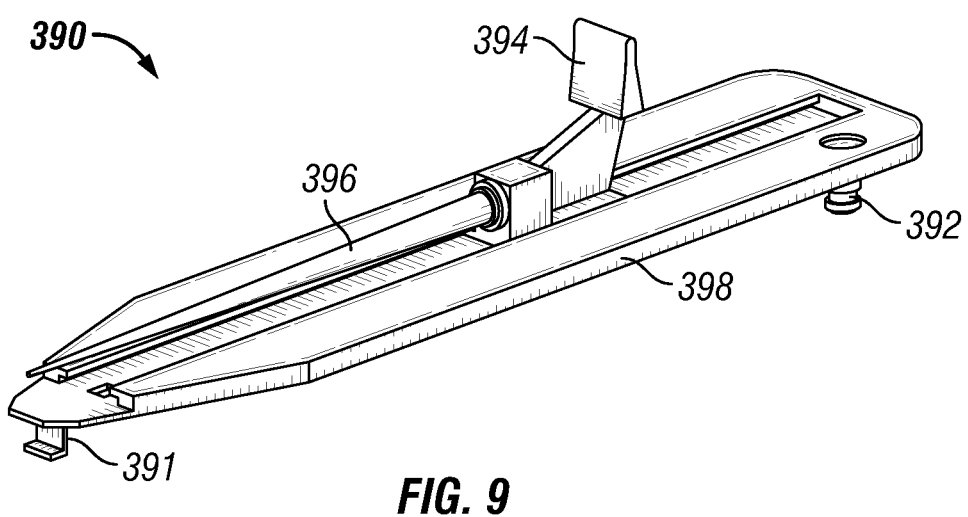
FIG. 9 is an illustrative implementation of an alignment cartridge.

In order to perform the alignment check on handheld robotic device 70, an alignment cartridge 390 is place in the device and handheld robotic device 70 on alignment cube 300. FIG. 9 is an illustrative implementation of an alignment cartridge 390. Alignment cartridge 390 may have similar interfaces and attachment points as the disposable cartridge, but does not contain any medical components. Similar to the disposable cartridge, an attachment tab and attachment slot (not shown) are utilized to attach alignment cartridge 390 to the handheld robotic device 70. Alignment cartridge 390 provides a stylet slider 394 attached to a stylet 396 that is the same length as the needle in the sterile disposable cartridge. Cartridge base 398 provides an opening that receives stylet slider 394 and allows stylet slider 394 to be advanced and retracted. Additionally, the back end of cartridge base 398 may provide a stylet interface similar to needle interface 215. This allows the handheld robotic device 70 to advance and retract stylet slider 394. For example, needle actuator 155 or sheath actuator 160 may be coupled to the stylet interface to allow needle motor 140 or sheath motor 145 to advance or retract stylet 396.

After filling the alignment cube 300 with water, the operator can perform the alignment check procedure. The operator may place handheld robotic device 70 on alignment cube 300. Display 50 may provide an image somewhat similar to FIG. 8. However, it should be noted that alignment cube 300 contains two vessel targets 325, 327 and target wires 330 and 335. As a result, two target vessels and several targets are also visible on the display. The operator can utilize thumb control 170 to center target cite 355 on shallow vessel target 325 at a depth of 30 mm and actuate trigger control 190 to advance stylet 396 into alignment cartridge 390. When the stylet 396 stops advancing, the distal end of stylet 396 should touch the intersection point at 30 mm between z-axis wire 335 and y-axis wire 330. Visual confirmation of this is made by looking through the viewing windows on the sides of the alignment cube. The operator can then repeat this procedure for deep vessel target 327 at 60 mm between the z-axis wire 335 and y-axis wire 330. If visual confirmation indicates that the stylet does not touch the intersection points of the wires at 30 mm or 60 mm, the robotic platform is recalibrated and adjusted for proper alignment.

Figure 10A:
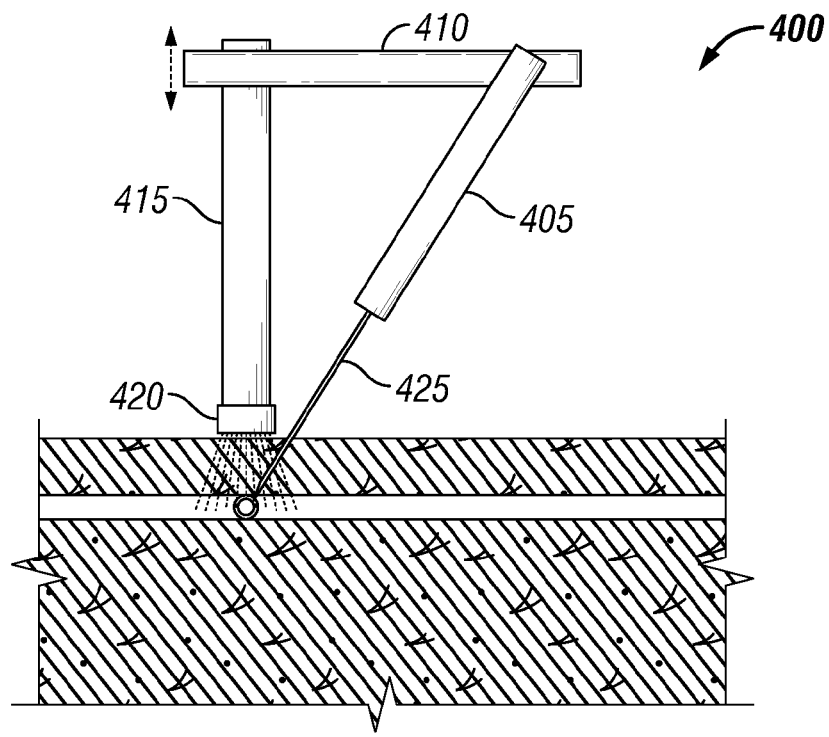
FIGS. 10A and 10B are illustrative implementations of a second arrangement for an insertion system.
Figure 10B:
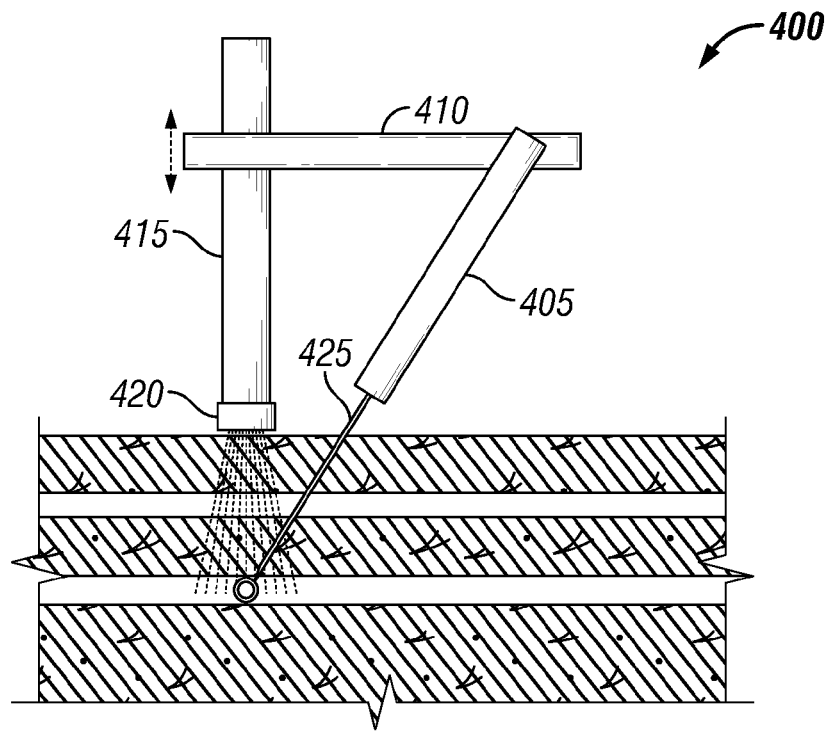

FIGS. 10A and 10B are illustrative implementations of a second arrangement for an insertion system 400. In insertion system 400, cartridge 405 is fixed at a predetermine angle. While cartridge 405 is shown independently attached to boom 410, in other implementations, cartridge 405 may be secured to fixed arm in a similar manner as to the cartridge carrier 110 shown in FIG. 4. Cartridge 405 may be coupled to adjustable boom 410, which may be adjusted vertically to achieve different target depths. Boom 410 is coupled to transducer arm 415. Transducer arm 415 provides a transducer housing for transducer 420. Needle 425 extends to a fixed predetermined length.

Figure 11A:
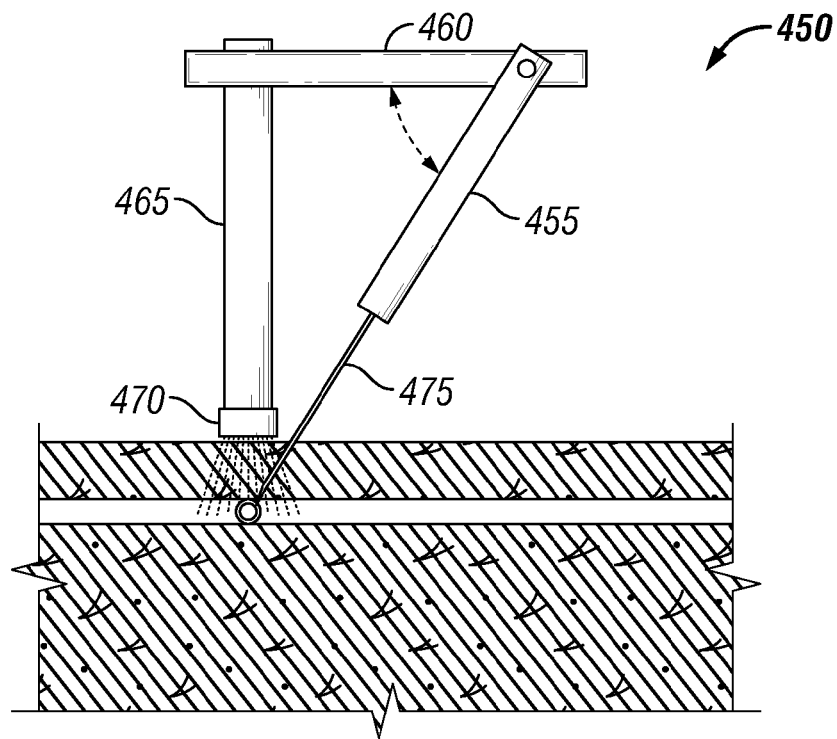
FIGS. 11A and 11B are illustrative implementations of a third arrangement for an insertion system.
Figure 11B:
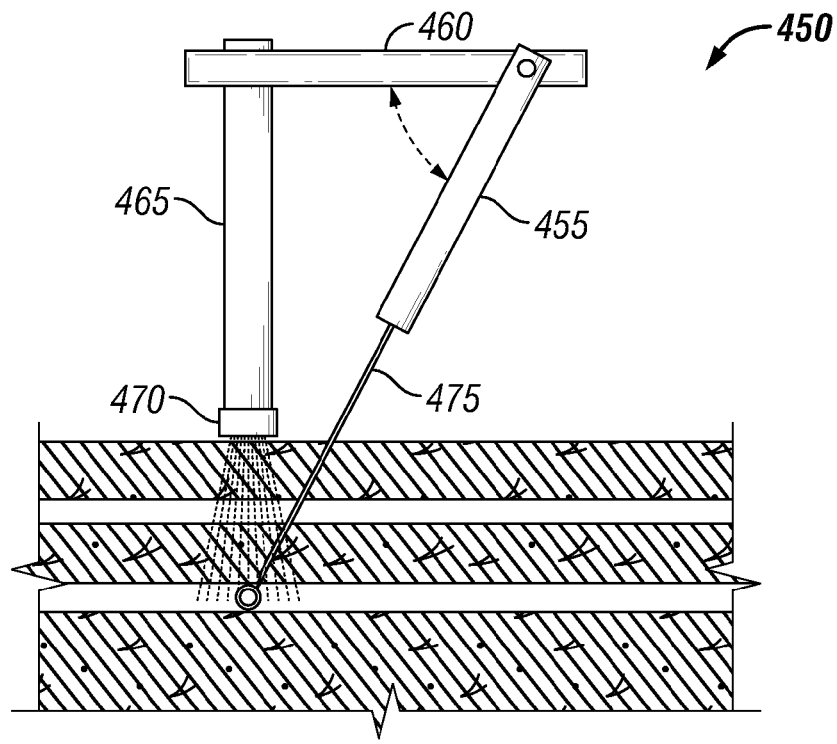

FIGS. 11A and 11B are illustrative implementations of a third arrangement for an insertion system 450. In insertion system 450, cartridge 455 has a variable angle in relation to boom 460. While cartridge 455 is shown independently attached to boom 460, in other implementations, cartridge 455 may be secured to fixed arm in a similar manner as to the cartridge carrier 110 shown in FIG. 4. In contrast to the previous implementation, boom 460 is a fixed height. Boom 460 is coupled to transducer arm 465, which provides a transducer housing for transducer 470. Needle 475 is a variable length needle. As the angle of cartridge 455 increase, the depth of insertion increases. The angle of cartridge 455 and length of needle 475 are adjusted to achieve a desired target depth.

Figure 12A:
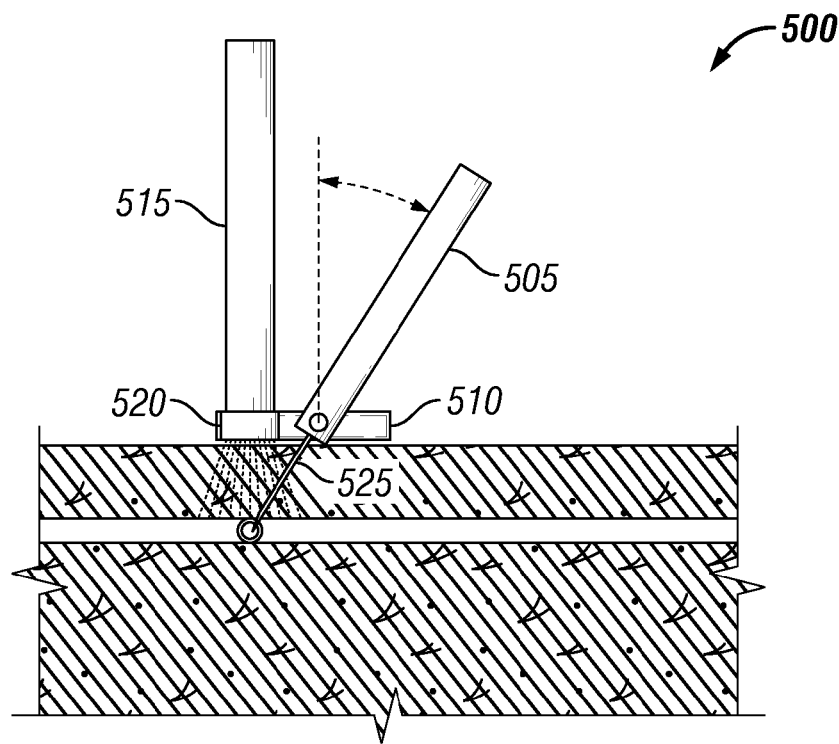
FIGS. 12A and 12B are illustrative implementations of a fourth arrangement for an insertion system.
Figure 12B:
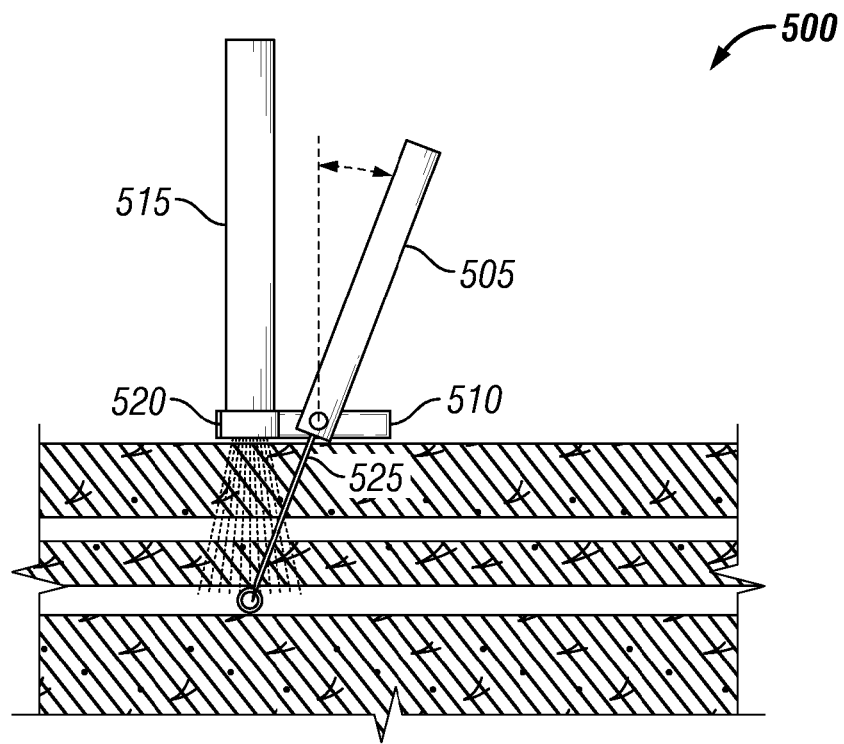

FIGS. 12A and 12B are illustrative implementations of a fourth arrangement for an insertion system 500. In insertion system 500, cartridge 505 has a variable angle in relation to boom 510. While cartridge 505 is shown independently attached to boom 510, in other implementations, cartridge 505 may be secured to fixed arm in a similar manner as to the cartridge carrier 110 shown in FIG. 4. Boom 510 is fixed near the bottom of transducer arm 515. Transducer arm 515 provides a transducer housing for transducer 520. Needle 525 is a variable length needle. As in the previous implementation, the angle of cartridge 505 and length of needle 525 are adjusted to achieve a desired target depth.

Figure 13A:
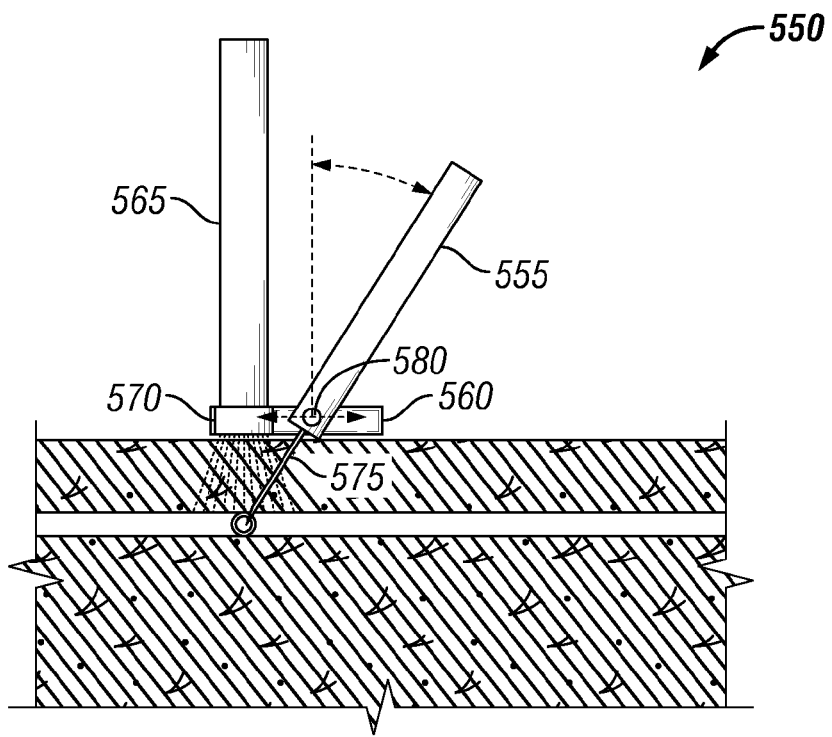
FIGS. 13A and 13B are illustrative implementations of a fifth arrangement for an insertion system.
Figure 13B:
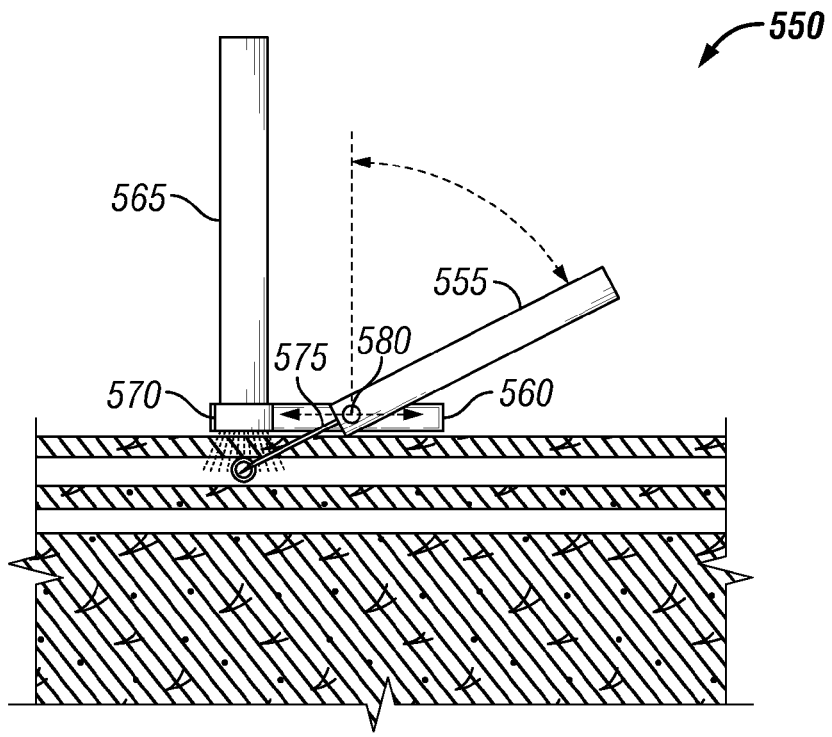

FIGS. 13A and 13B are illustrative implementations of a fifth arrangement for an insertion system 550. In insertion system 550, cartridge 555 has a variable angle in relation to boom 560. While cartridge 555 is shown independently attached to boom 560, in other implementations, cartridge 555 may be secured to fixed arm in a similar manner as to the cartridge carrier 110 shown in FIG. 4. Boom 560 is fixed near the bottom of transducer arm 565. Transducer arm 565 provides a transducer housing for transducer 570. Needle 575 is a fixed length needle. In contrast to the previous implementations, cartridge 555 has a variable pivot point 580 that can be moved along boom 560. The angle of cartridge 555 and variable pivot point 580 are adjusted to achieve a desired target depth.

Figure 14A:
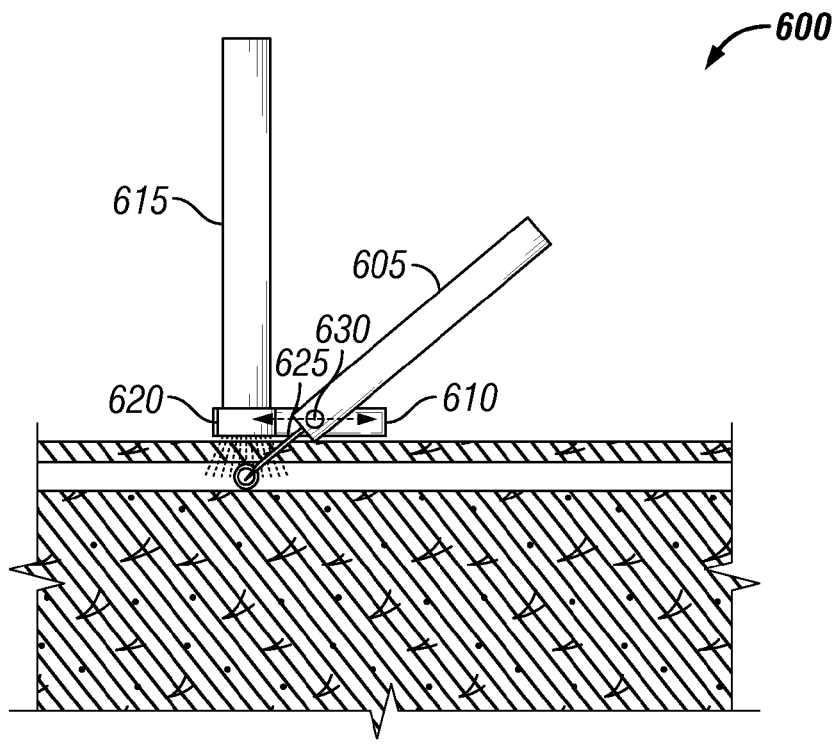
FIGS. 14A and 14B are illustrative implementations of a sixth arrangement for an insertion system.
Figure 14B:
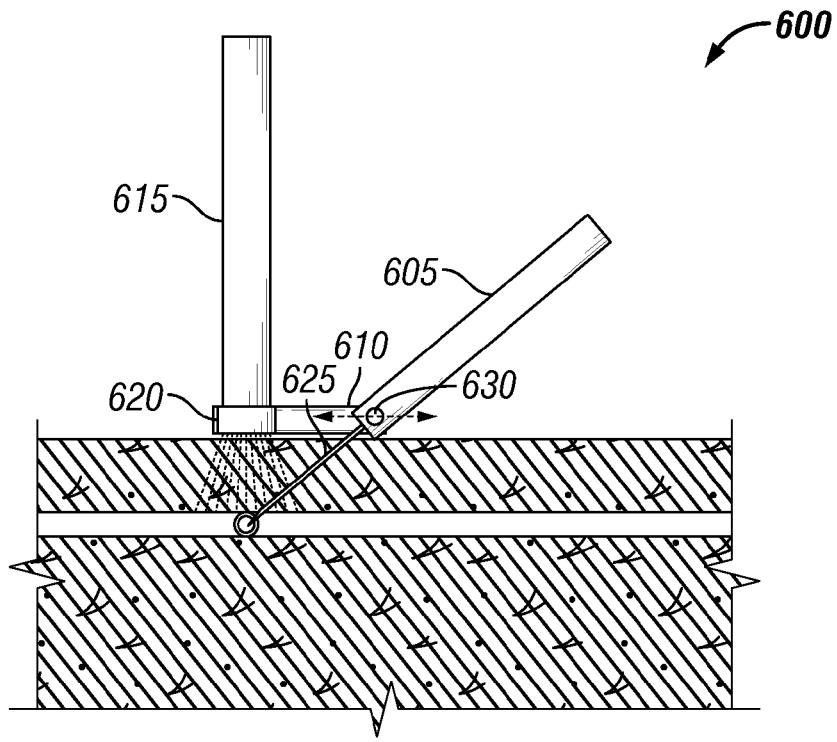

FIGS. 14A and 14B are illustrative implementations of a sixth arrangement for an insertion system 600. In insertion system 600, cartridge 605 has a fixed angle in relation to boom 610. While cartridge 605 is shown independently attached to boom 610, in other implementations, cartridge 605 may be secured to fixed arm in a similar manner as to the cartridge carrier 110 shown in FIG. 4. Boom 610 is fixed near the bottom of transducer arm 615. Transducer arm 615 provides a transducer housing for transducer 620. Needle 625 is a variable length needle. Cartridge 605 has a variable pivot point 630 that can be moved along boom 610. The variable pivot point 630 of cartridge 605 and length of needle 625 are adjusted to achieve a desired target depth. A depth scale (not shown) for insertion system 600 takes into account the a variable pivot point 630 and the amount needle 625 has been extended.

From the variety of arrangements discussed above, it should be noted that various arrangements may be also be suitable. For example, any suitable combination of a fixed/variable boom elevation, fixed/variable angle cartridge, fixed/variable needle length, and/or fixed/variable pivot point may be utilized.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. An apparatus to access a lumen of a vessel, the apparatus comprises:
   a handle provides a controller to operate the apparatus, wherein said handle is ergonomic to provide operation of said apparatus with a single hand;
   an image capturing instrument secured to the handle;
   a display secured to the handle, wherein images captured by the image capturing instrument are displayed on the display;
   a robotic platform coupled to the handle, wherein the robotic platform comprises,
      a body comprising an arc-like structure, wherein the handle and image capturing instrument are positioned at a center of the arc-like structure;
      a first motor coupled to the body, wherein the first motor adjust the robotic platform to achieve a target insertion depth;
      a cartridge carrier pivotally coupled to the body, wherein the robotic platform is adjustable to achieve the target insertion depth, and a pivot point of said cartridge carrier is positioned adjacent to said handle;
      a first actuator slideably coupled to said cartridge carrier, wherein said first motor adjusts a position of said first actuator, and said first actuator advances or retracts a needle or sheath;
      a stop bar positioned at a fixed position on said body; and
      an extension that extends from said first actuator, wherein said extension contacts said stop bar when said first actuator is advanced a predetermined length; and
   a disposable cartridge attached to the cartridge carrier, the disposable cartridge further comprises,
      the needle or sheath slideably coupled to the disposable cartridge, wherein the needle or sheath slides to extend to the target insertion depth.

2. The apparatus of claim 1, further comprises:
   a second motor coupled to a guidewire disposed in the disposable cartridge, wherein the guidewire is advanced by the second motor;
   a third motor coupled to the needle or sheath, wherein the needle or sheath is advanced and retracted by the third motor.

3. The apparatus of claim 2, further comprises:
   an actuator provided by the handle, wherein the actuator is actuated a first time to advance the needle or sheath into a target vessel and to advance the guidewire a first predetermined distance.

4. The apparatus of claim 3, wherein the actuator is actuated a second time to advance the guidewire fully into the target vessel and to advance the sheath into the target vessel.

5. The apparatus of claim 1, wherein cartridge carrier is rotatable around a pivot point coupling the cartridge carrier to the body.

6. The apparatus of claim 1, wherein the pivot point is adjustable, and the pivot point is laterally adjustable along the body.

7. The apparatus of claim 1, wherein the pivot point of the cartridge carrier is adjustable, and the pivot point is vertically adjustable along the body.

8. The apparatus of claim 1, further comprises:
   a target site displayed on the display, wherein the controller is utilized to select a target vessel by adjusting the target site onto a center of the target vessel.

9. The apparatus of claim 8, wherein the robotic platform automatically adjusts the first motor to achieve the target insertion depth in accordance with the target vessel selected.

10. A method for accessing a lumen of a vessel, the method comprises the steps of:
    attaching a disposable cartridge to a robotic platform, wherein the robotic platform comprises,
       a body comprising an arc-like structure, wherein a handle and an image capturing instrument are positioned at a center of the arc-like structure;
       a first motor coupled to the body, wherein the first motor adjust the robotic platform to achieve a target insertion depth;
       a cartridge carrier pivotally coupled to the body, wherein the robotic platform is adjustable to achieve the target insertion depth, and a pivot point of said cartridge carrier is positioned adjacent to said handle;
       the handle coupled to the robotic platform providing a controller for operating the robotic platform, wherein said handle is ergonomic to provide operation of said robotic platform with a single hand;
       a display secured to the handle, wherein images captured by the image capturing instrument are displayed on the display;
       a first actuator slideably coupled to said cartridge carrier, wherein said first motor adjusts a position of said first actuator, and said first actuator advances or retracts a needle or sheath;
       a stop bar positioned at a fixed position on said robotic platform; and
       an extension that extends from said first actuator, wherein said extension contacts said stop bar when said first actuator is advanced a predetermined length;
    placing the robotic platform over a target vessel, wherein said image capturing device generates an image of the target vessel on a display;
    selecting the target vessel on the display, wherein a depth of the target vessel is measured when selected; and
    actuating an actuator a first time, wherein actuating the actuator the first time causes the needle or a sheath provided in the disposable cartridge to advance to the depth measure and into the target vessel.

11. The method of claim 10, wherein the disposable cartridge attached to the cartridge carrier further comprises,
    the needle slideably coupled to the disposable cartridge, wherein the needle slides to extend to the target insertion depth; and
    the sheath slidably coupled to the disposable cartridge, wherein the sheath slides to extend to the target insertion depth.

12. The method of claim 11, wherein the robotic platform further comprises:
    a second motor coupled to a guidewire disposed in the disposable cartridge, wherein the guidewire is advanced by the second motor;
    a third motor coupled to the needle, wherein the needle is advanced and retracted by the third motor; and a fourth motor coupled to the sheath, wherein the sheath is advanced and retracted by the fourth motor.

13. The method of claim 10, wherein actuating the actuator the first time causes a guidewire to be advanced a first predetermined distance.

14. The method of claim 13, wherein actuating the actuator the second time causes a guidewire to be fully advanced into the target vessel and causes the needle to be retracted.

15. The method of claim 10, wherein the target vessel is selected by utilizing a controller to center a target site on a center of the target vessel.

16. The method of claim 15, wherein the robotic platform automatically adjust to achieve the target insertion depth in accordance with a selected target vessel.

17. The method of claim 10, further comprising entering a data entry mode, wherein patient information is entered in the data entry mode.

18. The method of claim 10, further comprising entering an operation mode, wherein images produced by the image capturing device are recorded in the operation mode.

19. An insertion system comprising:
a handle provides a controller to operate the system, wherein said handle is ergonomic to provide operation of said system with a single hand;
an image capturing instrument secured to the handle;
a display secured to the handle, wherein images captured by the image capturing instrument are displayed on the display;
a robotic platform comprising an arc-like structure coupled to the handle, wherein the handle and image capturing instrument are positioned at a center of the arc-like structure, and the robotic platform automatically adjust to achieve a target insertion depth;
a first motor coupled to the robotic platform, wherein the first motor adjust the robotic platform to achieve a target insertion depth;
a disposable cartridge pivotally attached to the robotic platform, wherein the disposable cartridge provides a sheath, a needle, or a guidewire, and the robotic platform inserts the sheath or needle to the target insertion depth, and a pivot point of said cartridge carrier is positioned adjacent to said handle;
a first actuator slideably coupled to said disposable cartridge, wherein said first motor adjusts a position of said first actuator, and said first actuator advances or retracts the needle or sheath;
a stop bar positioned at a fixed position on said robotic platform; and
an extension that extends from said first actuator, wherein said extension contacts said stop bar when said first actuator is advanced a predetermined length.

20. The apparatus of claim 19, wherein the controller is operated to select a target vessel, the robotic platform automatically adjust to achieve an insertion depth of said target vessel, and the robotic platform inserts the sheath or needle to the insertion depth of said target vessel.

* * * * *